(12) United States Patent
Kiyono et al.

(10) Patent No.: US 7,888,382 B2
(45) Date of Patent: Feb. 15, 2011

(54) COMBINED PHARMACEUTICAL PREPARATION FOR TREATMENT OF TYPE 2 DIABETES

(75) Inventors: Yuji Kiyono, Tokyo (JP); Yoshio Okubo, Tokyo (JP); Katsumi Hontani, Tokyo (JP); Imao Mikoshiba, Tokyo (JP); Kazuma Ojima, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 102 days.

(21) Appl. No.: 11/918,654

(22) PCT Filed: Apr. 18, 2006

(86) PCT No.: PCT/JP2006/308110

§ 371 (c)(1),
(2), (4) Date: Dec. 19, 2007

(87) PCT Pub. No.: WO2006/115115

PCT Pub. Date: Nov. 2, 2006

(65) Prior Publication Data

US 2009/0030063 A1    Jan. 29, 2009

(30) Foreign Application Priority Data

Apr. 20, 2005 (JP) .............................. 2005-121862
Jun. 7, 2005 (JP) .............................. 2005-166314

(51) Int. Cl.
*A01N 43/38* (2006.01)
*A01N 33/02* (2006.01)

(52) U.S. Cl. ....................................... 514/416; 514/659
(58) Field of Classification Search ................ 514/416
See application file for complete search history.

(56) References Cited

U.S. PATENT DOCUMENTS

| 2003/0040490 A1 | 2/2003 | Sugiyama et al. |
| 2004/0002544 A1 | 1/2004 | Makino et al. |
| 2005/0020654 A1* | 1/2005 | Pershadsingh et al. ...... 514/394 |
| 2005/0037980 A1* | 2/2005 | Rybczynski et al. .......... 514/23 |
| 2005/0197376 A1* | 9/2005 | Kayakiri et al. ............. 514/394 |

FOREIGN PATENT DOCUMENTS

| EP | 1 532 979 | 5/2005 |
| JP | 2001-316293 | 11/2001 |
| WO | 2007/033292 | 3/2007 |

OTHER PUBLICATIONS

International Search Report issued Jul. 5, 2006 in the International (PCT) Application of which the present application is the U.S. National Stage.
K. Ojima et al., "Pharmacological and Clinical Profile of Mitiglinide Calcium Hydrate (Glufast®), A New Insulinotropic Agent with Rapid Onset", Folia Pharmacol. Jpn. (Nippon Yakurigaku Zasshi), 2004, vol. 124, No. 4, pp. 245-255 (English Abstract enclosed).
K. Ojima et al., "Rapid Onset-Insulinotropic Effect of Mitiglinide Calcium Dihydrate (KAD-1229), A Novel Antipostprandial Hyperglycemic Agent", Jpn. Pharmacol Ther., 2004, vol. 32, No. 2, pp. 73-80.
R. F. Coniff et al., "Multicenter, Placebo-Controlled Trial Comparing Acarbose (BAY g 5421) with Placebo, Tolbutamide, and Tolbutamide-Plus-Acarbose in Non-Insulin-Dependent Diabetes Mellitus", The American Journal of Medicine, vol. 98, pp. 443-451, May 1995.
J. L. Chiasson et al., "Efficacy of Acarbose in the Treatment of Patients with Non-Insulin-Dependent Diabetes Mellitus: A Multicenter Controlled Clinical Trial", Annals of Internal Medicine, vol. 121, No. 12, pp. 928-935, Dec. 5, 1994.
European Office Action issued Jul. 29, 2010 in European Application No. 06 732 039.0 which is a foreign counterpart of the present application.

* cited by examiner

*Primary Examiner*—Sreeni Padmanabhan
*Assistant Examiner*—Timothy E Betton
(74) *Attorney, Agent, or Firm*—Wenderoth, Lind & Ponack, L.L.P.

(57) ABSTRACT

For controlling the condition of type 2 diabetes, a pharmaceutical including a combination of mitiglinide, a pharmacologically acceptable salt thereof or a hydrate thereof and an α-glucosidase inhibitor such as voglibose or acarbose, and a therapeutic method using the pharmaceutical are provided. The pharmaceutical according to the present invention has an extremely strong effect of decreasing a morning fasting blood glucose level, a postprandial blood glucose level and $HbA_{1C}$ of a patient with type 2 diabetes, and can improve glucose spike, insulin resistance and lipid metabolism.

7 Claims, 11 Drawing Sheets

COMBINED PHARMACEUTICAL PREPARATION FOR TREATMENT OF TYPE 2 DIABETES

TECHNICAL FIELD

The present invention relates to a pharmaceutical useful for treatment of type 2 diabetes. More specifically, the present invention relates to a pharmaceutical including a combination of mitiglinide and an α-glucosidase inhibitor.

BACKGROUND ART

A patient with type 2 diabetes is usually treated by giving a patient education for improving a life style such as a diet therapy or exercise therapy, medication including administration of an oral hypoglycemic agent or insulin, or a combination thereof.

As an oral hypoglycemic agent, an insulin secretagogue such as a sulfonylurea-based medicine, a sugar absorption regulator such as an α-glucosidase inhibitor, an insulin resistance improving agent such as a thiazolidine-based medicine or a biguanide-based medicine, or the like is used corresponding to a condition of the patient.

Recently, a rapid-acting insulin secretagogue such as nateglinide, repaglinide, mitiglinide calcium hydrate (product name: Glufast (registered trademark)) or the like, which is a kind of the oral hypoglycemic agent, has been proposed and received attention since a significant therapeutic effect thereof on improvement of a course of postprandial blood glucose has been shown. In a patient with type 2 diabetes, an increase in early-phase of insulin secretion after sugar loading, especially the increase within 30 minutes after the sugar loading is known to be significantly smaller than that of a healthy person. That is, while a blood glucose level of a healthy person gradually increases for 30 to 60 minutes after loading of glucose and then slowly decreases, when glucose is loaded to a patient with type 2 diabetes, a phenomenon of a precipitous increase in a blood glucose level within 30 to 90 minutes, which is called "glucose spike", is observed, because of low insulin secretion capability (Mebio, May 2003, Supplement "SYOKUGO KOUKETTO/IGT TO DAIKEKKANSYOUGAI (Postprandial Hyperglycemia/IGT and Macroangiopathy)" pp. 26-37). Therefore, a preferable drug exhibits efficacy in an early period after meal, especially within 30 to 60 minutes, to make a blood glucose course similar to that of a healthy person. The rapid-acting insulin secretagogue, particularly mitiglinide calcium hydrate is known to show a significant effect on improvement of a course of postprandial blood glucose. Mitiglinide calcium hydrate, however, is not known to effectively suppress glucose spike, especially glucose spike occurring within 1 hour after meal.

On the other hand, a combination therapy including administration of a combination of various drugs has been attempted to improve conditions of diabetes. As an example, a combined pharmaceutical including a combination of an α-glucosidase inhibitor and a non-sulfonylurea-based insulin secretagogue has been reported (Japanese Patent Publication No. 2001-316293). This report, however, does not describe specific effects of a combination of mitiglinide calcium hydrate and an α-glucosidase inhibitor, such as an extremely strong synergistic effect of decreasing a morning fasting blood glucose level, a postprandial blood glucose level and $HbA_{1C}$, suppression of glucose spike, and an effect of improving insulin resistance and lipid metabolism, as well as safety of the combination therapy, and the like.

In addition, a combination therapy of nateglinide and an α-glucosidase inhibitor has been reported to reproduce a blood glucose response comparable to that of a healthy person (Ryuzo Kawamori, "NAIBUNPI TONYOBYOKA (Endocrinology & Diabetology)", 12(6): 574-578, 2001). This report, however, does not include a detailed comparison between a monotherapy of nateglinide or the α-glucosidase inhibitor and the combination therapy, and there is no description regarding or suggesting the specific effects of combination as described above.

DISCLOSURE OF THE INVENTION

Problems to be Solved by the Invention

An object of the present invention is to provide a novel pharmaceutical including a combination of a plurality of pharmaceuticals for controlling a condition of type 2 diabetes, and a method for treatment of type 2 diabetes using the pharmaceutical.

Means for Solving the Problems

As a result of an earnest study in view of the above-described object, the inventors found that a pharmaceutical including a combination of mitiglinide calcium hydrate and an α-glucosidase inhibitor has an extremely good therapeutic effect on a patient with type 2 diabetes, in particular, significantly suppresses glucose spike occurring within 1 hour after meal, and that the pharmaceutical is safe, and completed the present invention.

Effect of the Invention

A pharmaceutical according to the present invention is a medicine for improving a course of postprandial blood glucose of a patient with type 2 diabetes, and is an extremely safe pharmaceutical having an extremely strong effect of decreasing a morning fasting blood glucose level, a postprandial blood glucose level and $HbA_{1C}$, and allowing improvement of glucose spike, insulin resistance and lipid metabolism.

BEST MODES FOR CARRYING OUT THE INVENTION

Figure 1:
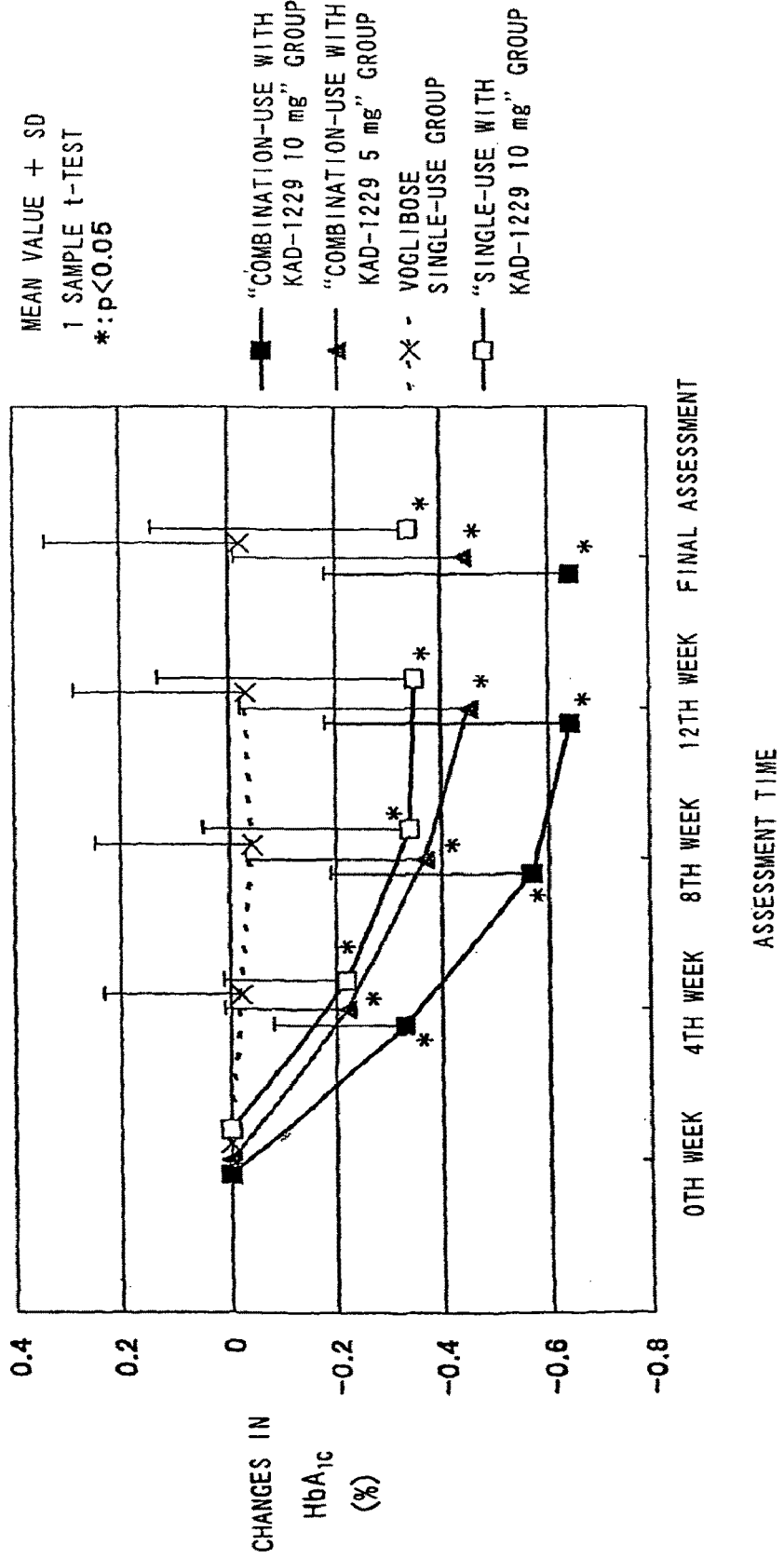
FIG. 1 shows courses of changes from a start time of a treatment period in $HbA_{1C}$ values.

Mitiglinide, a pharmacologically acceptable salt thereof or a hydrate thereof used in the present invention can be prepared by a method described in Japanese Patent Publication No. 4-356459. Among mitiglinide, a pharmacologically acceptable salt thereof or a hydrate thereof, mitiglinide calcium hydrate is preferably used. Commercially available mitiglinide calcium hydrate can be used. When mitiglinide calcium hydrate is used, a single dose thereof is usually within a range of 5-45 mg, preferably within a range of 5-20 mg, and especially 5-10 mg.

Examples of an α-glucosidase inhibitor include acarbose, voglibose, miglitol, emiglitate, and the like. Among these, acarbose or voglibose is preferred. Commercially available acarbose, voglibose or miglitol can be used. When acarbose is used, a single dose thereof is preferably within a range of 50-100 mg, and when voglibose is used, a single dose thereof is preferably within a range of 0.2-0.5 mg.

In this specification, the term "synergistic" means that an effect obtained by administration of a combination of mitiglinide, a pharmacologically acceptable salt thereof or a hydrate thereof and an α-glucosidase inhibitor is larger than a sum of effects of single administrations thereof.

A pharmaceutical according to the present invention is preferably administered 3 times a day before every meal (within 10 minutes before eating), in particular, immediately before meal (within 5 minutes before eating), in a single preparation (composition) including mitiglinide calcium hydrate and an α-glucosidase inhibitor, or in two kinds of preparations separately prepared from mitiglinide calcium hydrate and an α-glucosidase inhibitor, which are administered concurrently or at an interval of time.

As compositions including mitiglinide calcium hydrate and an α-glucosidase inhibitor, oral agents such as tablets, capsules, powders or granules are preferable. Tablets, for example, can be prepared by mixing mitiglinide calcium hydrate and the α-glucosidase inhibitor as active ingredients with an excipient such as lactose, saccharose, corn starch, D-mannitol, crystalline cellulose or calcium carbonate; a disintegrant such as carmellose or low substituted hydroxypropylcellulose; a binder such as alpha starch, gum arabic or hydroxypropylcellulose; a lubricant such as talc, magnesium stearate or calcium stearate; and the like as appropriate, and then forming by compression.

When the pharmaceutical according to the present invention is implemented as two different kinds of preparations, administrations of mitiglinide, a pharmacologically acceptable salt thereof or a hydrate thereof and the α-glucosidase inhibitor should be performed concurrently or at a very short interval such as within 10 minutes, which is therefore preferably described in a package insert or a sales brochures or the like of, for example, a commercially available pharmaceutical including mitiglinide calcium hydrate as an effective component (product name: Glufast (registered trademark)). A kit including a preparation containing mitiglinide calcium hydrate and a preparation containing an α-glucosidase inhibitor is also preferable.

A patient as a therapeutic object of the pharmaceutical according to the present invention is preferably a patient whose blood glucose could not be sufficiently controlled by a dietary therapy, and who requires introduction of medication and has $HbA_{1C}$ of at least 6.5%, in particular, $HbA_{1C}$ of at least 6.5% even with administration of the α-glucosidase inhibitor.

EXAMPLES

The present invention is described below in more detail based on Examples. The scope of the present invention, however, is not limited by the embodiments.

(Hardness Test)

A hardness of a test tablet was measured using a durometer (TS-75N, manufactured by Okada Seiko Co., Ltd.). The test was performed using 3 tablets to obtain a mean value.

(Disintegration Test)

A disintegration test was performed according to a disintegration test of Japanese Pharmacopoeia General Test using purified water at 37° C. as test liquid. The test was performed using 3 tablets to obtain a mean value.

Example 1

Mitiglinide calcium hydrate: 10.0 mg

Voglibose: 0.2 mg

Lactose: 137.0 mg

Corn starch: 60.0 mg

Crystalline cellulose: 55.0 mg

Low substituted hydroxypropylcellulose: 12.0 mg

Hydroxypropylcellulose: 2.5 mg

Magnesium stearate: 3.3 mg (Total 280.0 Mg/Tablet)

After mixing 0.5 g of mitiglinide calcium hydrate, 6.85 g of lactose (produced by HMS Co., Ltd.), 3 g of corn starch (produced by Nihon Shokuhin Kako Co., Ltd.), 2.75 g of crystalline cellulose (produced by Asahi Kasei Corporation), and 0.6 g of low substituted hydroxypropylcellulose (produced by Shin-Etsu Chemical Co., Ltd.) together in a mortar for 3 minutes, 3.375 g of purified water containing 0.01 g of voglibose and 0.125 g of hydroxypropylcellulose (produced by Nippon Soda Co., Ltd.) was gradually added thereto. Thereafter, 1.26 g of purified water was gradually added with agitation to perform granulation. Resulting granules were dried in a shelf drier (DN64, manufactured by Yamato Scientific Co., Ltd.) at 60° C. for 2 hours, and then sieved with a No. 30 sieve. To 11 g of the granules, 0.131 g of magnesium stearate (produced by Taihei Chemical Industrial Co., Ltd.) was added and mixed for 30 seconds. This mixture was compressed to prepare tablets using a single stroke tabletting machine (N-30E, manufactured by Okada Seiko Co., Ltd.) under conditions of a tablet weight of 280 mg, φ9.5 mm 10.5 R round shape, and a compression pressure of 13 kN/pounder. The tablet had a hardness of 68 N and a disintegration time of 3.1 minutes.

Example 2

Mitiglinide calcium hydrate: 5.0 mg
Voglibose: 0.2 mg
Lactose: 111.4 mg
Corn starch: 50.0 mg
Crystalline cellulose: 27.5 mg
Low substituted hydroxypropylcellulose: 6.0 mg
Hydroxypropylcellulose: 2.5 mg
Magnesium stearate: 2.4 mg
(Total 205.0 Mg/Tablet)

After mixing 0.25 g of mitiglinide calcium hydrate, 5.57 g of lactose (produced by HMS Co., Ltd.), 2.5 g of corn starch (produced by Nihon Shokuhin Kako Co., Ltd.), 1.375 g of crystalline cellulose (produced by Asahi Kasei Corporation), and 0.3 g of low substituted hydroxypropylcellulose (produced by Shin-Etsu Chemical Co., Ltd.) together in a mortar for 3 minutes, 3.375 g of purified water containing 0.01 g of voglibose and 0.125 g of hydroxypropylcellulose (produced by Nippon Soda Co., Ltd.) was gradually added with agitation to perform granulation. Resulting granules were dried in the shelf drier (DN64, manufactured by Yamato Scientific Co., Ltd.) at 60° C. for 2 hours, and then sieved with a No. 30 sieve. To 8 g of the granules, 0.095 g of magnesium stearate (produced by Taihei Chemical Industrial Co., Ltd.) was added and mixed for 30 seconds. This mixture was compressed to prepare tablets using the single stroke tabletting machine (N-30E, manufactured by Okada Seiko Co., Ltd.) under conditions of a tablet weight of 205 mg, φ8 mm 12 R round shape, and a compression pressure of 10 kN/pounder. The tablet had a hardness of 62 N and a disintegration time of 4.3 minutes.

Test Examples 1, 2 and Comparative Examples 1, 2

Clinical trials as follows were performed with double-blind, parallel group trial on patients with type 2 diabetes.

(Inclusion Criteria)

Type 2 diabetic patients of at least 20 years old whose blood glucose could not be sufficiently controlled by a dietary therapy and who requires introduction of medication and has $HbA_{1C}$ of at least 6.5% and less than 8.5%.

(Investigational Drugs)

(1) 5 mg tablet of mitiglinide calcium hydrate (hereafter also referred to as "KAD-1229")
(2) placebo tablet of KAD-1229 5 mg tablet
(3) 10 mg tablet of KAD-1229
(4) placebo tablet of KAD-1229 10 mg tablet
(5) 0.2 mg tablet of voglibose
(6) placebo tablet of voglibose 0.2 mg tablet (Method of Administration)

A 0.2 mg tablet of voglibose was orally administered 3 times a day immediately before every meal (within 5 minutes before eating) for 16 weeks (an observation period: a non-blind trial period). Thereafter, investigational drugs distributed as Table 1 were orally administered 3 times a day immediately before every meal (within 5 minutes before eating) for 12 weeks (a treatment period: a double-blind trial period). Administration of the investigational drugs after meal was not allowed, and administration was not performed when the meal was not taken.

TABLE 1

| Administration Group | | Investigational Drugs |
|---|---|---|
| Example 1 | KAD-1229 (10 mg) and Voglibose | (2) + (3) + (5) |
| Example 2 | KAD-1229 (5 mg) and Voglibose | (1) + (4) + (5) |
| Comparative Example 1 | Voglibose | (2) + (4) + (5) |
| Comparative Example 2 | KAD-1229 (10 mg) | (2) + (3) + (6) |

The following items were assessed during and after the period of administration.

(1) $HbA_{1C}$ Values

FIG. 1 shows courses of changes from a start time of the treatment period in $HbA_{1C}$ values during the clinical trials.

Further, in the courses of $HbA_{1C}$ value, when an insulin secretagogue such as sulfonylurea is used, a decreasing tendency of the $HbA_{1C}$ value declines and sometimes the value even increases as an administration period becomes longer. In a combined administration group, however, the $HbA_{1C}$ value can be controlled well during long-term administration.

Figure 2:
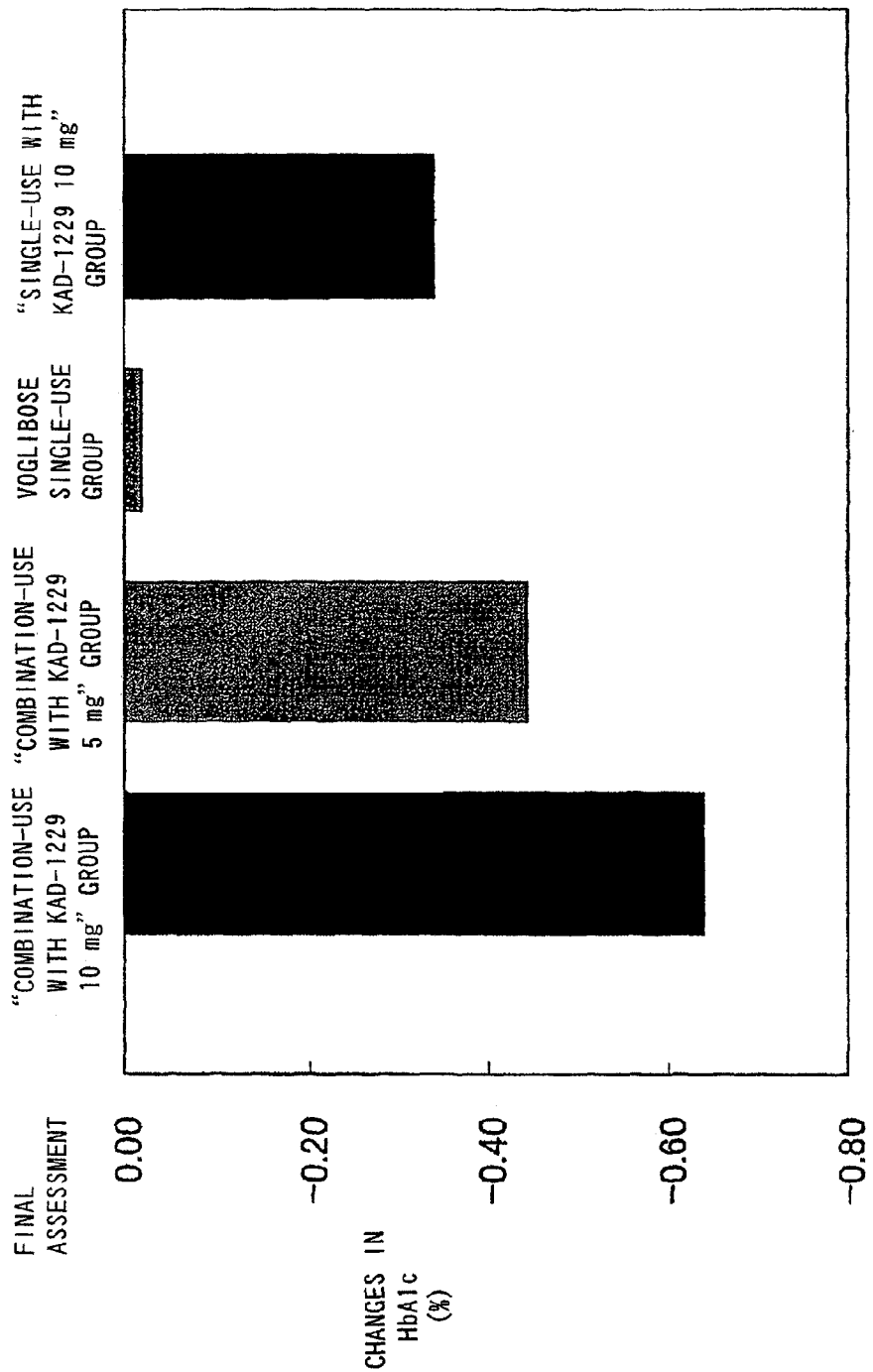
FIG. 2 shows changes from the start time of the treatment period in $HbA_{1C}$ at a time of a final assessment.

FIG. 2 shows changes in $HbA_{1C}$ values at the end of the treatment period. Each of combined administration groups shows a synergistically decreased $HbA_{1C}$ value as compared to single administration groups.

Figure 3:
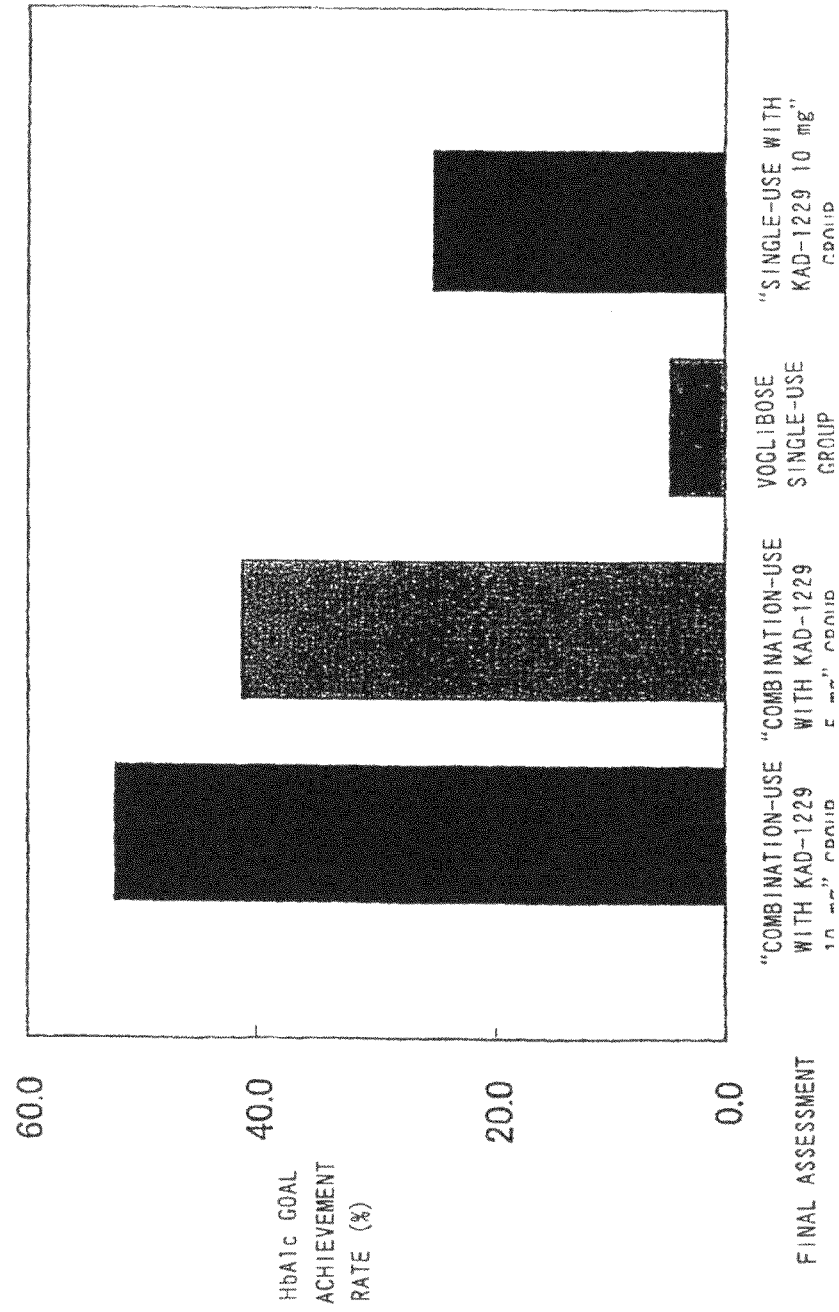
FIG. 3 shows $HbA_{1C}$ goal achievement rates at the time of the final assessment from the start time of the treatment period.

FIG. 3 shows rates of patients whose $HbA_{1C}$ values at final assessment decreased to less than 6.5%. The combined administration group is shown to have an obviously higher rate in the $HbA_{1C}$ value than that of the single administration group.

Figure 4:
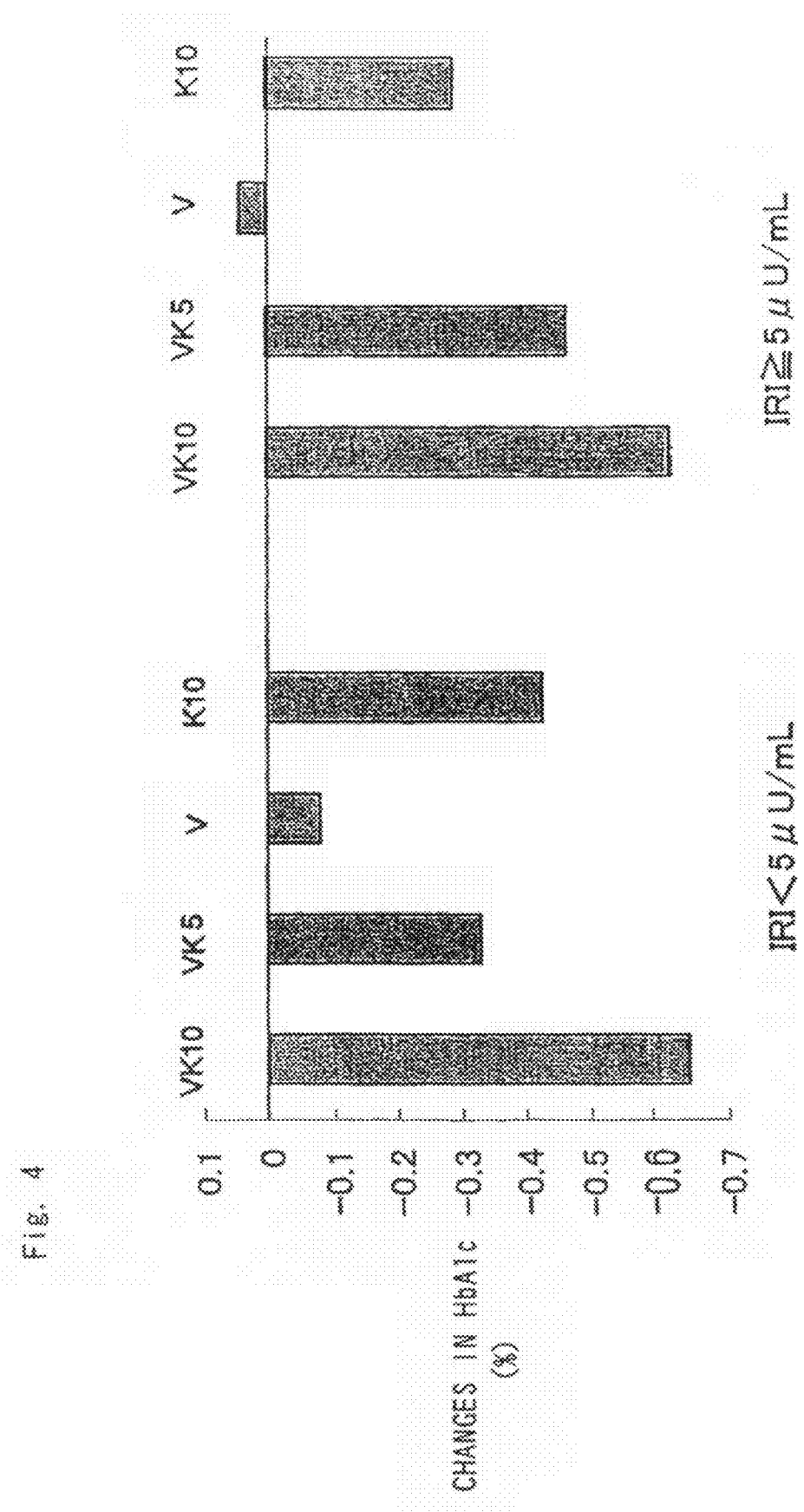
FIG. 4 shows changes from the start time of the treatment period in $HbA_{1C}$ value at the time of the final assessment, which are stratified with a blood insulin value (IRI) of 5 μU/mL at the start time of the treatment period. VK10 indicates Test Example 1, VK5 indicates Test Example 2, V indicates Comparative Example 1, K10 indicates Comparative Example 2, and IRI indicates a blood insulin value.

FIG. 4 shows changes in $HbA_{1C}$ values in patients without an insulin resistance tendency having blood insulin values (IRI) of less than 5 µU/mL and in patients with an insulin resistance tendency having the values of at least 5 µU/mL.

Figure 5:
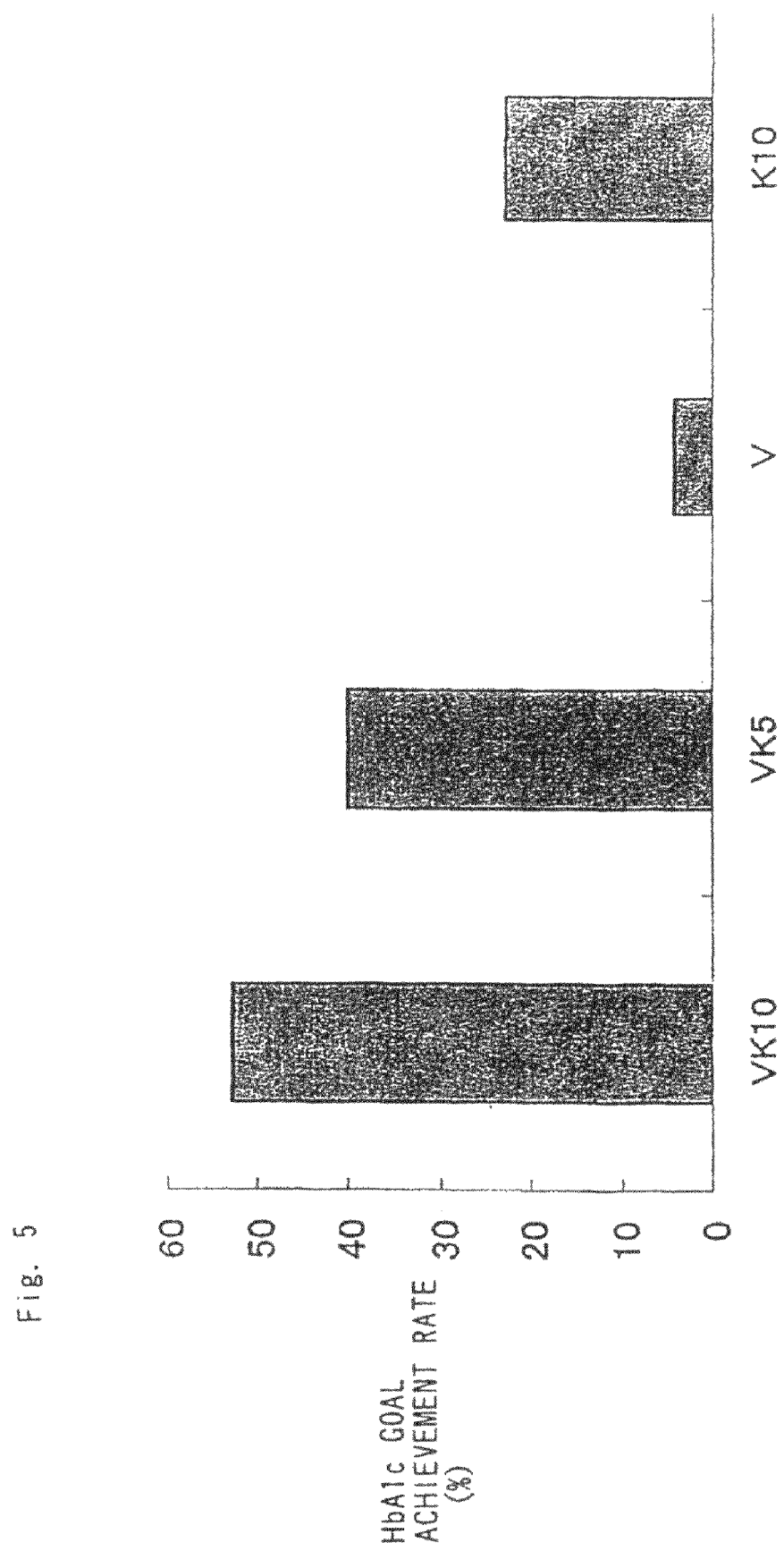
FIG. 5 shows $HbA_{1C}$ goal achievement rates in a patient stratum with the blood insulin value at the start time of the treatment period of at least 5 μU/mL. VK10 indicates Test Example 1, VK5 indicates Test Example 2, V indicates Comparative Example 1, and K10 indicates Comparative Example 2.

FIG. 5 shows $HbA_{1C}$ goal achievement rates in patients having the blood insulin values of at least 5 µU/mL.

It can be seen that combined administration of KAD-1229 and voglibose to patients with the insulin resistance tendency having the blood insulin values of at least 5 µU/mL can control $HbA_{1C}$ values very well as compared to single administration of KAD-1229 or voglibose. That is, the goal achievement rate of treatment in patients with insulin resistance is markedly increased by the combined administration. This means that the insulin resistance of the patients was improved by the combined administration of KAD-1229 and voglibose.

(2) Morning Fasting Plasma Glucose Levels

Figure 6:
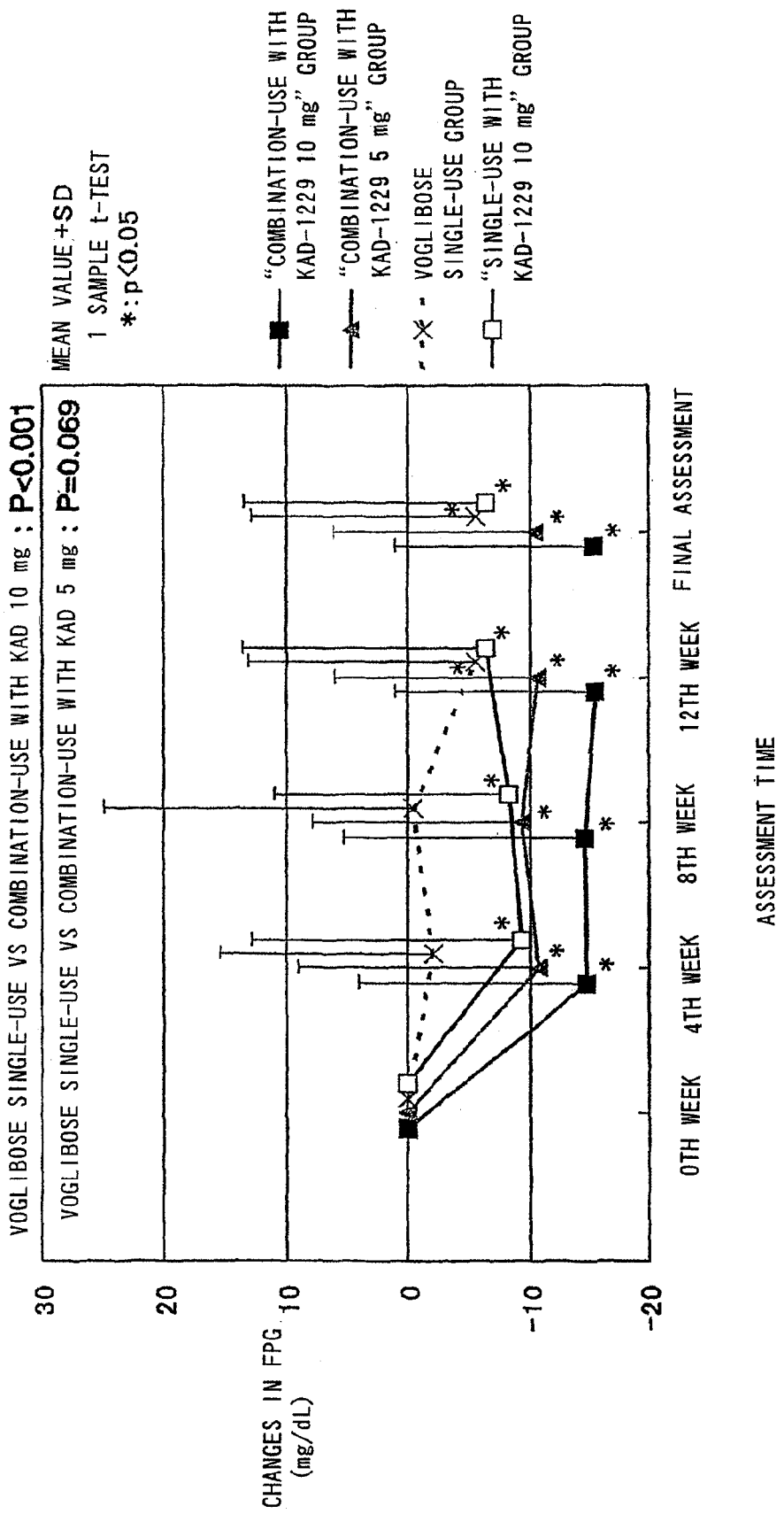
FIG. 6 shows courses of changes from the start time of the treatment period in morning fasting plasma glucose level (FPG).

FIG. 6 shows courses of changes from the start time of the treatment period in morning fasting plasma glucose levels (FPG). In the combined administration groups, the morning fasting plasma glucose levels were synergistically decreased as compared to the single administration groups.

(3) 1-Hour and 2-Hour Postprandial Blood Glucose Levels

Figure 7:
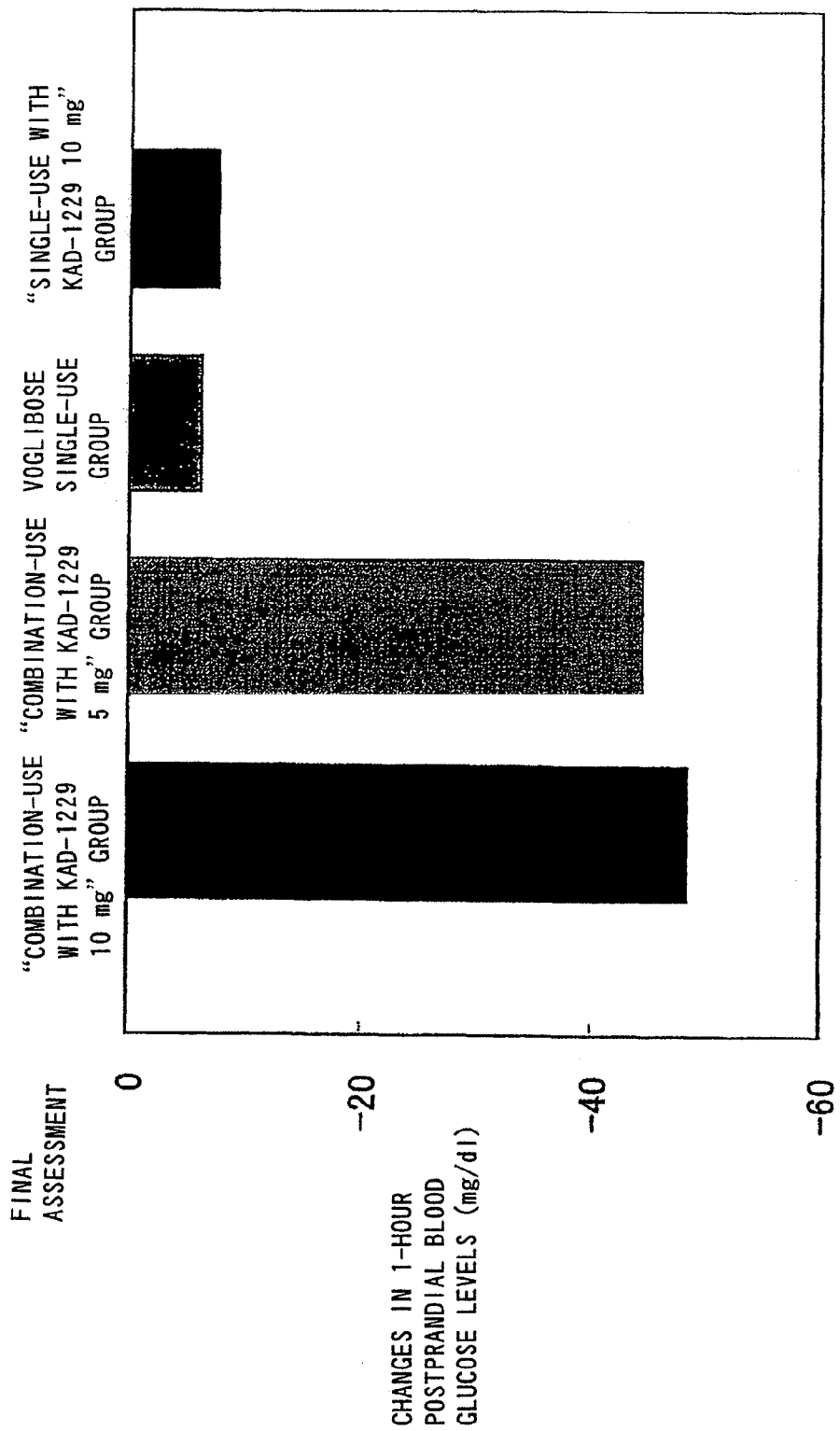
FIG. 7 shows changes from the start time of the treatment period in 1-hour postprandial blood glucose levels at the time of the final assessment.
Figure 8:
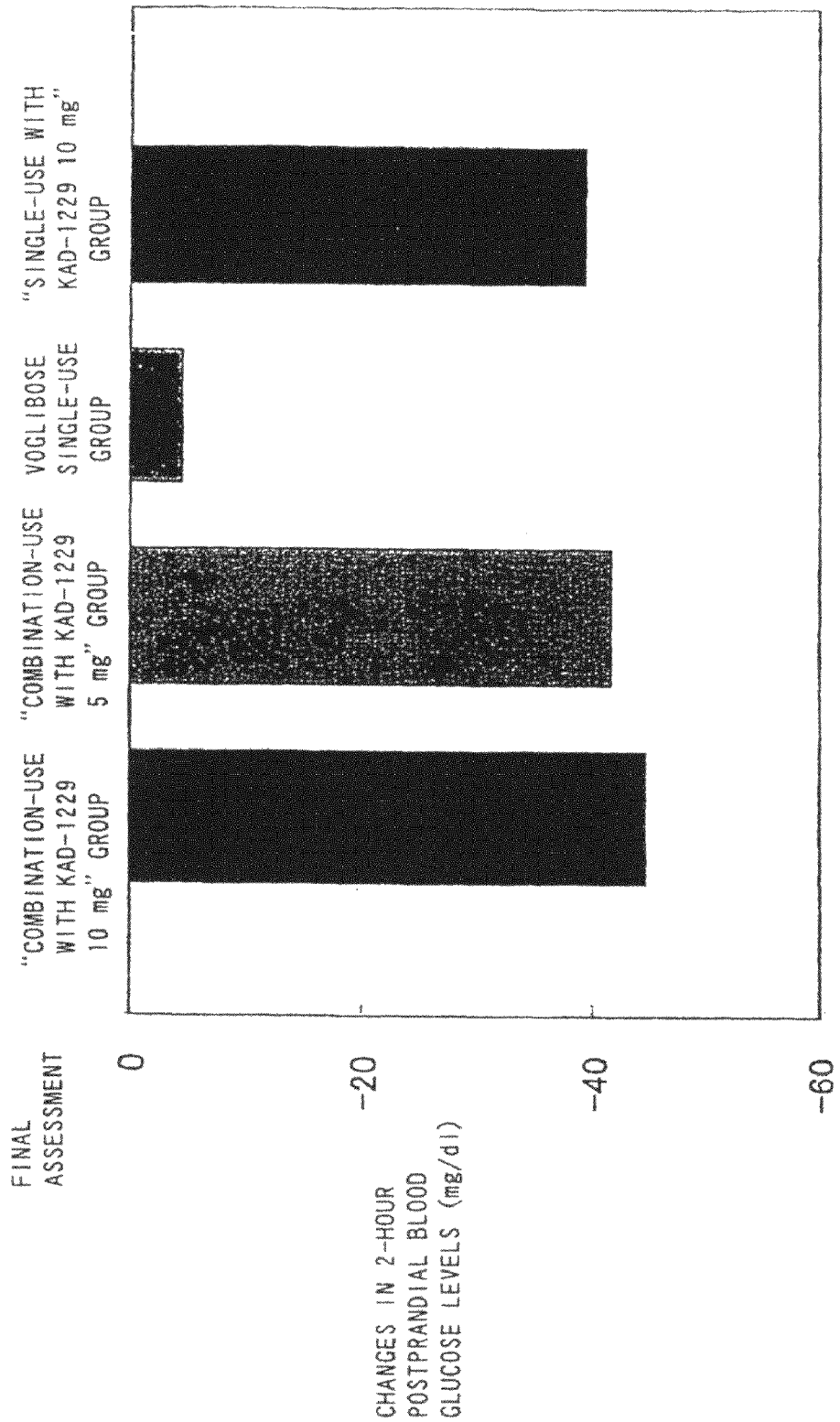
FIG. 8 shows changes from the start time of the treatment period in 2-hour postprandial blood glucose levels at the time of the final assessment.

FIGS. 7 and 8 show changes from the start time of the treatment period in 1-hour and 2-hour postprandial blood glucose levels at the time of the final assessment. In the combined administration groups, the blood glucose levels were synergistically decreased as compared to the single administration groups. In addition, the 1-hour postprandial blood glucose levels indicate that glucose spikes in the combined administration groups are significantly suppressed as compared to the single administration groups.

(4) Lipid Parameters

Figure 9:
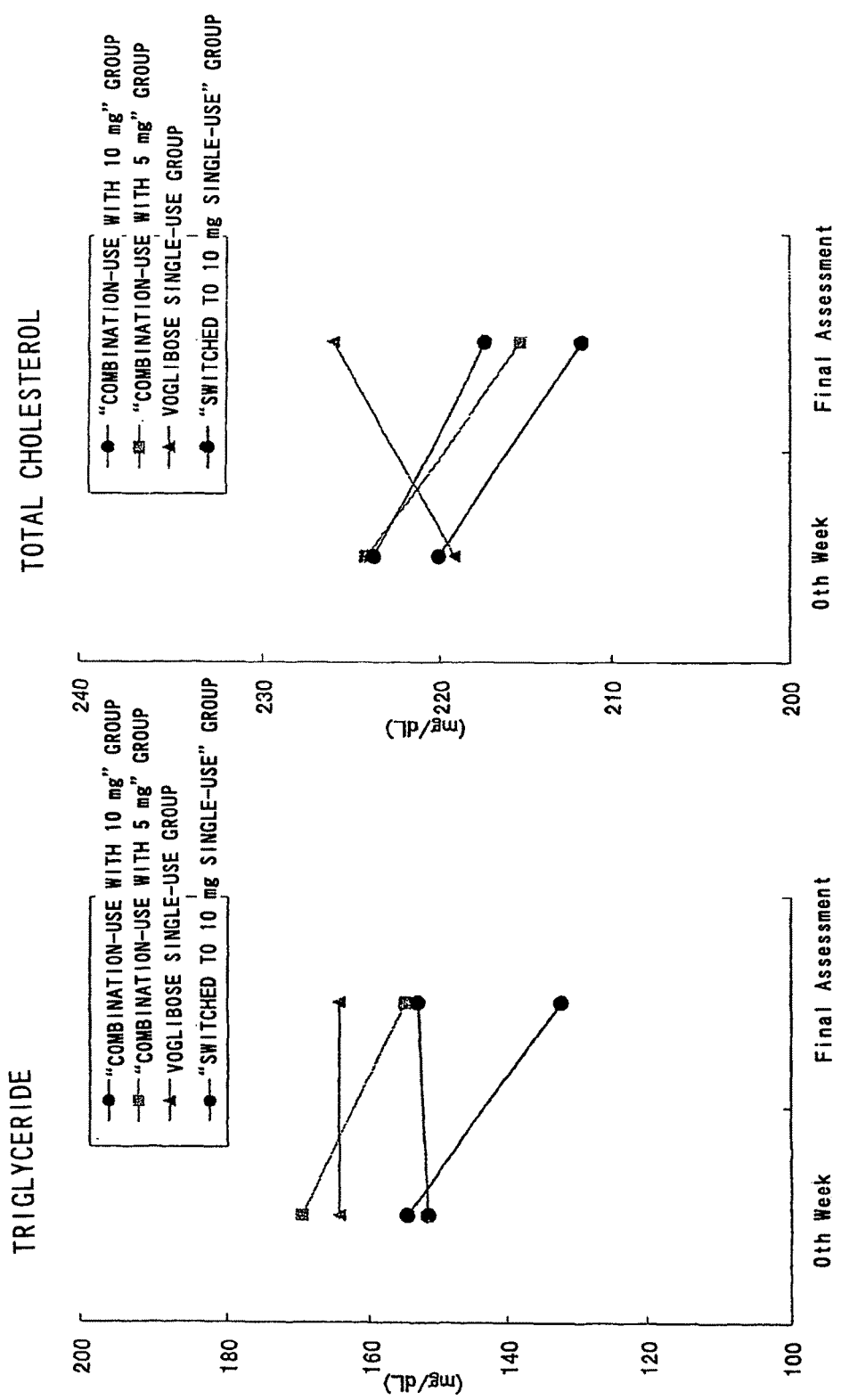
FIG. 9 shows courses of lipid parameters from the start time of the treatment period.

FIG. 9 shows changes in triglyceride (TG) values and total cholesterol (TC) values in patients with hyperlipemia as a complication. It can be seen that the TG values and the TC values are markedly decreased in the combined administration group as compared to the single administration group.

(5) Hypoglycemic Symptoms

Incidence rates of hypoglycemic symptoms during the treatment period were 6.9% in Test Example 1, 3.3% in Test Example 2, 1.1% in Comparative Example 1, and 3.9% in Comparative Example 2.

(6) Gastrointestinal Disorders

Incidence rates of gastrointestinal disorders during the treatment period were 9.8% in Test Example 1, 6.6% in Test Example 2, 10.1% in Comparative Example 1, and 6.8% in Comparative Example 2. The incidence rate of gastrointestinal disorders in each combined administration group is lower than that of the single administration group of voglibose. This means that KAD-1229 administration mitigated the gastrointestinal disorders caused by voglibose.

Test Example 3

A dose of 0.2-0.3 mg of voglibose or 50-100 mg of acarbose was orally administered 3 times a day immediately before every meal (within 5 minutes before eating) for 16 weeks (an observation period). Then, a dose of 10 mg of KAD-1229 was orally administered together with voglibose or acarbose 3 times a day immediately before every meal (within 5 minutes before eating) for 28 weeks (a treatment period).

The dose of KAD-1229 was increased to 20 mg when a patient having $HbA_{1C}$ of at least 7.0% at a start time of the treatment period had $HbA_{1C}$ of at least 7.0% 12 weeks later, and when a patient having $HbA_{1C}$ of at least 6.5% and less than 7.0% at the start time of the treatment period had $HbA_{1C}$ of at least 6.5% 12 weeks later. In addition, the amount of KAD-1229 could be decreased at any time.

Figure 10:
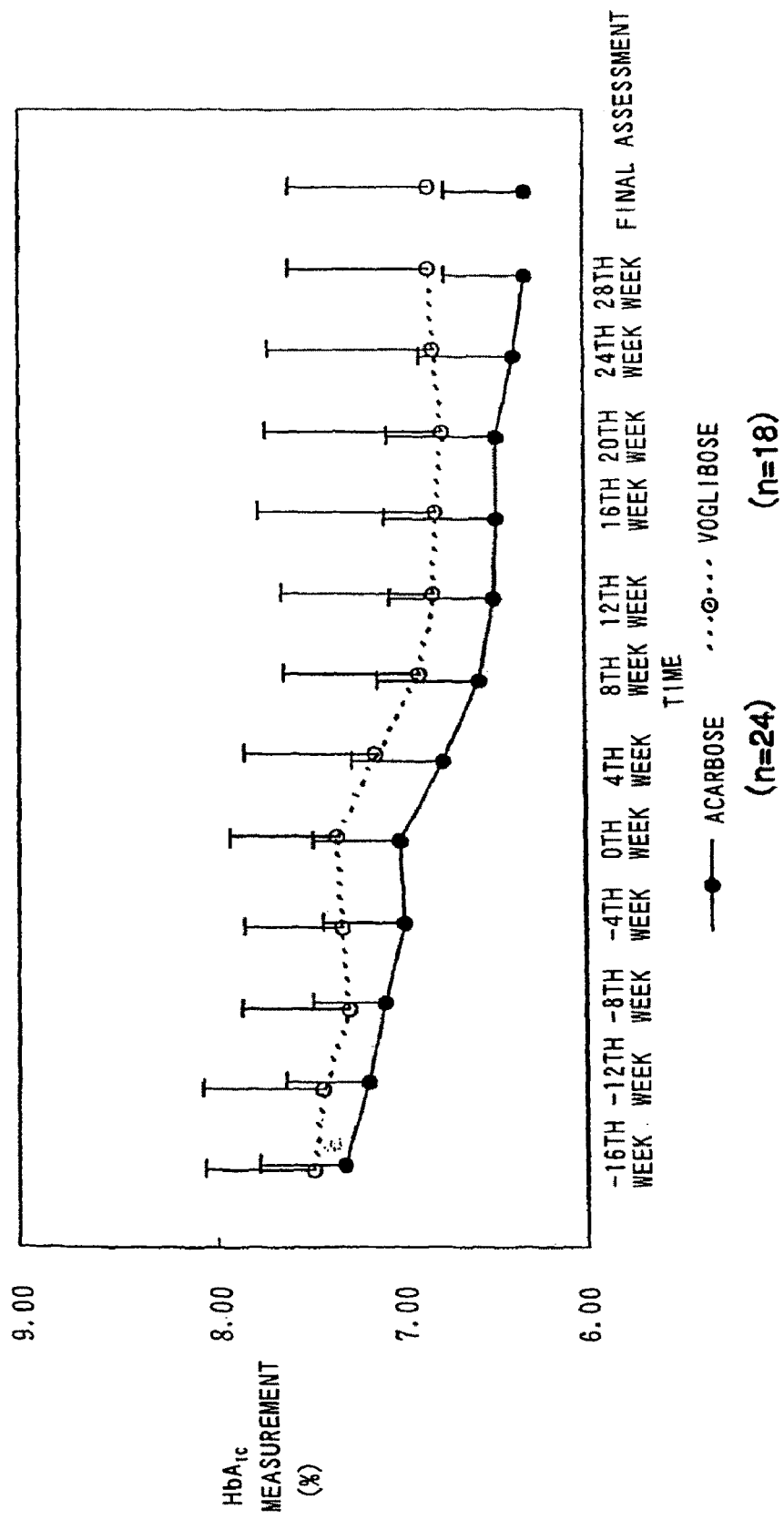
FIG. 10 shows courses of $HbA_{1C}$ measurements from a start time of an observation period in a combined administration test with acarbose or voglibose.

FIG. 10 shows courses of $HbA_{1C}$ measurements from a start time of the observation period. An effect of a combination of KAD-1229 and voglibose or a combination of KAD-1229 and acarbose on $HbA_{1C}$ measurements was similar to each other.

Safety of the combination therapy was confirmed since there was no serious side effect observed during the clinical trials described above. As described above, use of a combination of mitiglinide, a pharmacologically acceptable salt thereof or a hydrate thereof and an α-glucosidase inhibitor such as voglibose can obtain an extremely high therapeutic effect, can decrease a dose of the α-glucosidase inhibitor required to attain the same effect, and can markedly increase a goal achievement rate of treatment. Therefore, an incidence rate of a side effect of the α-glucosidase inhibitor, in particular, a gastrointestinal disorder can be decreased, or a condition thereof can be mitigated.

Test Example 4

1) Animals

Male Wistar rats purchased from Japan SLC, Inc. were used in this test.

2) Oral Sucrose Tolerance Test

An oral sucrose tolerance test was performed using 7-week-old rats.

The rats were fasted for at least 16 hours and received oral administration of 2.5 mL/kg of a prepared tested substance or a vehicle (0.5% CMC solution), followed by oral administration of 5 mL/kg of 0.5 g/mL sucrose solution (2.5 g/kg). Blood was drawn from a rat tail vein immediately before administration and 0.25 and 0.5 hours after loading. A plasma glucose concentration was measured using a Glucose CII-test Wako (Wako Pure Chemical Industries, Ltd.).

A dose of the tested substance was converted from a usual dose of each drug for a type 2 diabetic patient (mitiglinide: 10 mg, nateglinide: 120 mg, repaglinide: 1 mg). As for nateglinide, a converted value of 12 mg was changed to 20 mg to be set as a dose, considering an effect thereof. Data processing was performed as follows.

1) Assessment Item

An area under the plasma glucose concentration-time curve from a time before sucrose loading to 0.5 hours after sucrose loading ($AUC_{0-0.5}$ hr) was set as an assessment item. Blood glucose $AUC_{0-0.5}$ hr was calculated from plasma glucose concentrations with a trapezoidal rule using the area under the plasma glucose concentration-time curve. For each data, a mean value and a standard error were calculated using Excel and displayed to one decimal place.

2) Software Used

Excel (Microsoft Corp.) and GraphPad Prism 3.0 (GraphPad Software Inc.) were used to aggregate and calculate data, to make diagrams and the like. For a statistical analysis of the data, SAS System Version 8.2 (SAS Institute Inc.) and a coupled program thereof, Preclinical Package Version 5.0 (SAS Institute Japan), were used.

3) Statistical Analysis

Comparisons among the groups of combinations of mitiglinide, nateglinide and repaglinide with voglibose were performed using a parametric Dunnett's multiple comparison test. A significance level (a two-tailed test) of less than 5% was adopted.

Figure 11:
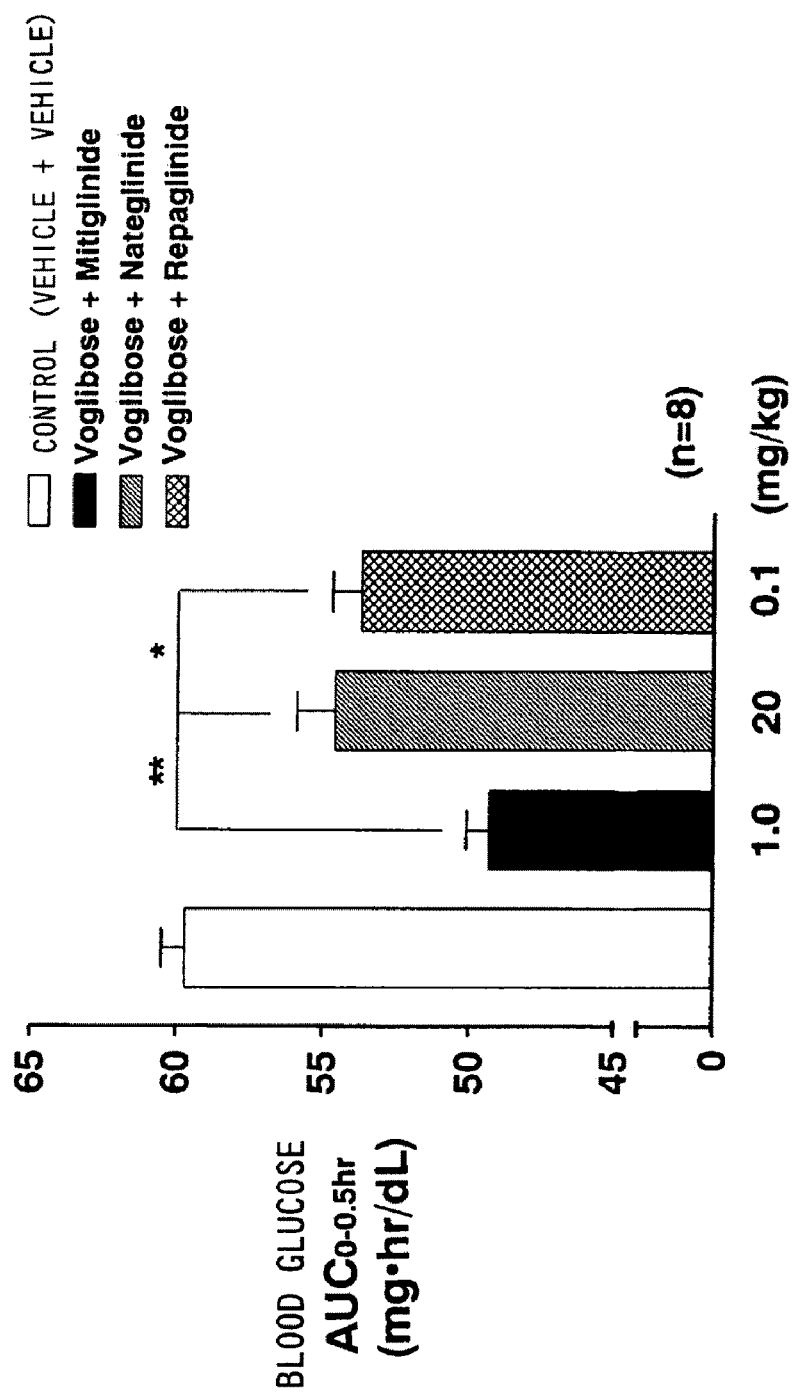
FIG. 11 shows a result of a combined administration test of nateglinide, mitiglinide or repaglinide with voglibose.

The result is shown in FIG. 11. Among rapid-acting insulin secretagogues, mitiglinide showed a strong blood glucose decreasing effect within a very short time in combination with the α-glucosidase inhibitor as compared to nateglinide or repaglinide.

INDUSTRIAL APPLICABILITY

A pharmaceutical including a combination of mitiglinide, a pharmacologically acceptable salt thereof or a hydrate thereof and an α-glucosidase inhibitor is an extremely superior pharmaceutical having a high therapeutic effect and a high level of safety.

The invention claimed is:

1. A method for decreasing a morning fasting blood glucose level, wherein a combined pharmaceutical consisting essentially of (1) mitiglinide calcium hydrate and (2) an α-glucosidase inhibitor is orally administered before every meal to a patient with type 2 diabetes having a hemoglobin $A_{1C}$ ($HbA_{1C}$) value of at least 6.5% even with administration of the α-glucosidase inhibitor selected from voglibose and acarbose for improving a course of postprandial blood glucose, wherein a single dose of mitiglinide calcium hydrate is 5-45 mg.

2. A method for decreasing hemoglobin $A_{1C}$ ($HbA_{1C}$), wherein a combined pharmaceutical consisting essentially of (1) mitiglinide calcium hydrate and (2) an α-glucosidase inhibitor is orally administered before every meal to a patient with type 2 diabetes having a hemoglobin $A_{1C}$ ($HbA_{1C}$) value of at least 6.5% even with administration of the α-glucosidase inhibitor selected from voglibose and acarbose for improving a course of postprandial blood glucose, wherein a single dose of mitiglinide calcium hydrate is 5-45 mg.

3. A method for suppressing glucose spike which is an increase of blood glucose level occurring within 1 hour after a meal, wherein a combined pharmaceutical consisting essentially of (1) mitiglinide calcium hydrate and (2) an α-glucosidase inhibitor is orally administered before every meal to a patient with type 2 diabetes having a hemoglobin $A_{1C}$ ($HbA_{1C}$ value of at least 6.5% even with administration of the α-glucosidase inhibitor selected from voglibose and acarbose for improving a course of postprandial blood glucose, wherein a single dose of mitiglinide calcium hydrate is 5-45 mg.

4. The method according to any one of claims 1 to 3, wherein a single dose of voglibose is within a range of 0.2-0.5 mg, and a single dose of acarbose is within a range of 50-100 mg.

5. The method according to any one of claims 1 to 3, wherein a single dose of mitiglinide calcium hydrate is 5-10 mg, and a single dose of voglibose as the α-glucosidase inhibitor is 0.2 mg.

6. The method according to any one of claims 1 to 3, wherein said combined pharmaceutical is a composition.

7. The method according to any one of claims 1 to 3, wherein said combined pharmaceutical is two kinds of preparations prepared separately of (1) mitiglinide calcium hydrate and (2) an α-glucosidase inhibitor selected from voglibose and acarbose.

* * * * *